United States Patent [19]
Harding et al.

[11] Patent Number: 5,945,360
[45] Date of Patent: Aug. 31, 1999

[54] BIOSOLUBLE POT AND MARBLE-DERIVED FIBERGLASS

[75] Inventors: Foster Laverne Harding; Jon Frederick Bauer, both of Castle Rock; Harry Hand Russell, III, Evergreen; Xiaojie Xu, Littleton, all of Colo.

[73] Assignee: Johns Manville International, Inc., Denver, Colo.

[21] Appl. No.: 08/827,571

[22] Filed: Mar. 28, 1997

[51] Int. Cl.[6] ..................................... C03C 13/06
[52] U.S. Cl. ................... 501/36; 501/35; 501/72
[58] Field of Search ................... 501/35, 36, 66, 501/69, 72

[56] References Cited

U.S. PATENT DOCUMENTS

| | | |
|---|---|---|
| 3,811,853 | 5/1974 | Bartholomew et al. . |
| 3,840,359 | 10/1974 | Lazet . |
| 4,510,252 | 4/1985 | Potter . |
| 4,542,106 | 9/1985 | Sproull . |
| 4,615,988 | 10/1986 | Le Moigne et al. ................ 501/36 |
| 5,055,428 | 10/1991 | Porter . |
| 5,108,957 | 4/1992 | Cohen et al. ...................... 501/35 |
| 5,250,488 | 10/1993 | Thelohan et al. . |
| 5,332,698 | 7/1994 | Nyssen et al. .................... 501/35 |
| 5,332,699 | 7/1994 | Olds et al. ........................ 501/36 |
| 5,401,693 | 3/1995 | Bauer et al. . |
| 5,429,996 | 7/1995 | Kaneko . |
| 5,583,080 | 12/1996 | Guldberg et al. . |
| 5,591,453 | 1/1997 | Ducheyne et al. . |

*Primary Examiner*—Karl Group
*Attorney, Agent, or Firm*—Robert D. Touslee

[57] ABSTRACT

Glass compositions suitable for pot and marble fiberization display excellent chemical resistance to both acids and moisture while being highly biosoluble at the same time. The glass compositions are characterized by ratios of components which are reflective of acid resistance, biosolubility, and moisture resistance. Preferred glasses have a difference between HTV ($10^3$ poise) and liquidus greater than 500° F., and a biodissolution greater than about 350 ng/cm²/hr.

24 Claims, No Drawings

BIOSOLUBLE POT AND MARBLE-DERIVED FIBERGLASS

TECHNICAL FIELD

The present invention pertains to fiberglass products prepared from glass compositions suitable for fiberization by the pot and marble process. The glass fibers exhibit enhanced biosolubility while maintaining other desirable properties.

DESCRIPTION OF THE RELATED ART

Fiberglass has a myriad of uses, including the reinforcement of polymer matrix composites; preparation of thermoformable intermediate products for use as headliners and hoodliners in vehicles; air and water filtration media; and sound and thermal insulation products. The preparation and/or subsequent processing of such materials often involves handling steps which result in cut or broken fibers which may be inhaled. As it is impractical or impossible to remove such fibers from the body, it has become important to create glass compositions which exhibit high degrees of biosolubility, i.e. which are rapidly solubilized in biological fluids.

If high biosolubility were the only factor which need be considered, a solution to the biosolubility problem would be rapidly attained. However, in addition to being biosoluble, glass fibers must also possess a number of other physical and chemical characteristics. For example, in many applications such as in battery separators, high chemical (e.g. acid) resistance is required. As can be readily imagined, high chemical resistance and high biosolubility are largely conflicting characteristics.

Glass fibers must also be strong and moisture-resistant. If moisture weakens glass fibers appreciably, their applicability to many uses suffers. Weakened glass fibers not only possess less than desired tensile strength and modulus, but also break and fracture more easily, thus increasing the risk of inhalation, etc. By the same token, moisture resistant glass fibers which have low strength to begin with also do not fulfill many requirements. For example, building insulation is shipped in compressed form. If the glass fibers of the insulation product are weak or brittle, many fibers will be broken during compression, not only increasing the number of small fibers which are bioavailable, but also producing an inferior product which may not recover a sufficient amount of its pre-compressed thickness. Strong fibers which are not moisture resistant also exhibit a great deal of breakage, especially under humid storage, as illustrated hereinafter. Finally, glass fibers must be prepared from glass compositions which can be economically processed.

The two principle methods of glass wool fiber production are the pot and marble process and the centrifugal or "rotary" process. In the latter, molten glass enters a centrifugal spinner from the forehearth of a glass melting furnace. As the centrifugal spinner rotates, relatively large diameter glass strands stream from orifices located in the spinner's periphery. These large diameter strands immediately contact an intense hot gas jet produced by burners located around the spinner. The hot gas attenuates the large diameter strands into fine, elongated fibers, which may be collected on a moving belt.

As glass is an amorphous rather than crystalline "solid", crystallization in the melt or during fiberization will disrupt the fiber glass forming process with disastrous results. In the rotary process, the glass ingredients are first melted in a glass melter prior to their entry into the forehearth. Thus, the feed to the forehearth is high temperature, molten glass. From the forehearth, the molten glass fed to the spinner is cooled to the HTV (high temperature viscosity) or "fiberization" temperature. Because the forehearth is fed with hot, molten glass, and the temperature of the glass in the forehearth is above the HTV, the difference in temperature between the HTV and liquidus ("$\Delta T$"), the temperature which defines the boundary of crystallization, may be quite small in the rotary process.

In the pot and marble process, relatively large diameter "primary" strands of glass (primaries) exude from holes located in the bottom of the pot. Because room temperature marbles are continuously or incrementally added to the pot, numerous locations will exist within the pot where the temperature might fall below the liquidus temperature, thermodynamically favoring crystallization and disrupting the process. To ensure that the process is not disrupted, glass compositions must be used which exhibit a significant difference, minimally 300° F., between the HTV and liquidus temperatures. Thus, glass compositions formulated for the rotary process, having low $\Delta T$, are not suitable for use in pot and marble process.

The primaries exiting the pot from the pot and marble process are flame attenuated rather than hot gas attenuated, thus exposing the glass fibers to higher temperatures than in the rotary process. These higher temperatures cause a loss of the more volatile compounds of the glass composition from the outside of the fibers, resulting in a "shell" which has a different composition than the fiber interior. As a result, the biosolubility of glass fibers prepared from pot and marble fiberglass is not the same as that derived from the rotary process. As glass fibers must necessarily dissolve from the fiber ends or the cylindrical exterior, more highly resistant shell will drastically impede the biodissolution rate.

SUMMARY OF THE INVENTION

It has now been surprisingly discovered that glass fibers of enhanced biosolubility may be prepared from glass compositions suitable for pot and marble processing, which exhibit minimally about a 350° F. difference in HTV and liquidus, and which have well defined formulations meeting both narrow mol percentage composition as well as meeting each of three specific "C-ratios" which govern chemical resistance, moisture resistance, and biosolubility.

DESCRIPTION OF THE PREFERRED EMBODIMENTS

The subject invention glasses have HTV and liquidus which are suitable for production of glass fibers in the pot and marble process. Such glass generally must have an HTV ($10^3$ poise) of 1800° F. to 2100° F., preferably 1900° F. to 2000° F., and exhibit a liquidus which is minimally about 350° F., preferably 425° F., and more preferably 500° F. or more lower than the HTV. These characteristics are necessary to prepare glass fibers economically on a continuous basis.

The glass composition must fall within the following range of composition, in mol percent:

| | |
|---|---|
| $SiO_2$ | 66–69.7 |
| $Al_2O_3$ | 0–2.2 |
| RO | 7–18 |

-continued

| | |
|---|---|
| $R_2O$ | 9–20 |
| $B_2O_3$ | 0–7.1 | where $R_2O$ is an alkali metal oxide and RO is an alkaline earth metal oxide. $R_2O$ is preferably $Na_2O$ in most substantial part, while RO may be MgO and/or CaO, preferably both, in a molar ratio of MgO/CaO of 1:3 to 3:1, more preferably 2:3 to 3:2. The chemical behavior of the glass is dictated by three ratios which the glass composition must meet, C(acid), C(bio), and C(moist). These ratios are defined compositionally as follows, all amounts being in mol percent:

$$C(acid) = [SiO_2]/([Al_2O_3]+[B_2O_3]+[R_2O]+[RO])$$

$$C(bio) = ([SiO_2]+[Al_2O_3])/([B_2O_3]+[R_2O]+[RO])$$

$$C(moist) = ([SiO_2]+[Al_2O_3]+[B_2O_3])/([R_2O]+[RO]).$$

In these ratios, C(acid) is the ratio which pertains to chemical resistance in acid environments, C(bio) is the ratio which is most closely linked to biosolubility, and C(moist) is the ratio which relates to retention of properties in moist environments. It is desired that C(acid) and C(moist) be as large as possible, while C(bio) should be as low as possible. At the same time, the HTV and liquidus of the overall composition must be suitable for glass fiber processing. It has been found that pot and marble glass of high biosolubility, while yet maintaining other necessary physical properties such as chemical resistance and moisture resistance, is obtained when C(acid)≧1.95, C(bio)≦2.30, and C(moist)≧2.40.

Preferably, the biosoluble fiberglass of the subject invention has a composition which falls within the following ranges (in mol percent):

| | |
|---|---|
| $SiO_2$ | 66–69.0 |
| $Al_2O_3$ | 0–2.2 |
| RO | 7–16 |
| $R_2O$ | 9–19 |
| $B_2O_3$ | 0–7.1 |

Most preferably, the biosoluble glass fibers of the subject invention have a composition which falls within the following most preferred range:

| | |
|---|---|
| $SiO_2$ | 66–68.25 |
| $Al_2O_3$ | 0–2.2 |
| RO | 7–13 |
| $R_2O$ | 11–18 |
| $B_2O_3$ | 0–7.1 |

With respect to the performance characteristics of the glass fibers of the subject invention, it is preferred that C(acid) be greater than or equal to 2.00; C(bio) be less than or equal to 2.23, more preferably less than or equal to 2.20; and that C(moist) be greater than or equal to 2.50, preferably greater than or equal to 2.60. As discussed previously, it is most desirable that C(acid) and C(moist) be as high as possible. For example, C(moist) values of 3.00 or greater are particularly preferred. It should be noted also, that the various C-ratios are independent in the sense that a more preferred glass need not have all "more preferred" C-ratios.

Acid resistance may be measured by battery industry standard tests. For example, a typical test involves addition of 5 grams of nominally 3 μm diameter fiber in 50 mL of sulfuric acid having a specific gravity of 1.26. Following refluxing for 3 hours, the acid phase may be separated by filtration and analyzed for dissolved metals or other elements.

The procedure used to evaluate biodissolution rate is similar to that described in Law et al. (1990). The procedure consists essentially of leaching a 0.5 gram aliquant of the candidate fibers in a synthetic physiological fluid, known as Gamble's fluid, or synthetic extracellular fluid (SEF) at a temperature of 37° C. and a rate adjusted to achieve a ratio of flow rate to fiber surface area of 0.02 cm/hr to 0.04 cm/hr for a period of up to 1,000 hours duration. Fibers are held in a thin layer between 0.2 μm polycarbonate filter media backed by plastic support mesh and the entire assembly placed within a polycarbonate sample cell through which the fluid may be percolated. Fluid pH is regulated to 7.4+0.1 through the use of positive pressure of 5% $CO_2$/95% $N_2$ throughout the flow system.

Elemental analysis using inductively coupled plasma spectroscopy (ICP) of fluid samples taken at specific time intervals are used to calculate the total mass of glass dissolved. From this data, an overall rate constant could be calculated for each fiber type from the relation:

$$k = [d_o \rho (1-(M/M_o)^{0.5})]/2t$$

where k is the dissolution rate constant in SEF, $d_o$ the initial fiber diameter, ρ the initial density of the glass comprising the fiber, $M_o$ the initial mass of the fibers, M the final mass of the fibers ($M/M_o$=the mass fraction remaining), and t the time over which the data was taken. Details of the derivation of this relation is given in Leineweber (1982) and Potter and Mattson (1991). Values for k may be reported in $ng/cm^2/hr$ and preferably exceed a value of 150. Replicate runs on several fibers in a given sample set show that k values are consistent to within 3 percent for a given composition.

Data obtained from this evaluation can be effectively correlated within the sample set chosen—dissolution data used to derive k's were obtained only from experimental samples of uniform (3.0 μm) diameter and under identical conditions of initial sample surface area per volume of fluid per unit time, and sample permeability. Data was obtained from runs of up to 30 days to obtain an accurate representation of the long term dissolution of the fibers. Preferred biodissolution rate constants in $ng/cm^2/hr$ are greater than 150 $ng/cm^2/hr$, preferably greater than 200 $ng/cm^2/hr$, more preferably greater than 300 $ng/cm^2/hr$, and most preferably greater than 400 $ng/cm^2/hr$.

Having generally described this invention, a further understanding can be obtained by reference to certain specific examples which are provided herein for purposes of illustration only and are not intended to be limiting unless otherwise specified.

EXAMPLES

Comparative C1 and C2

C-ratios are calculated for a conventional C-glass (chemically resistant glass) and a "soluble" glass as disclosed in Examples 1a and 2b in Table 1 of U.S. Pat. No. 5,055,428. The glass composition is in weight percent. HTV ($10^3$ poise) and liquidus are as reported in the '428 patent.

TABLE 1

| | Comparative Example 1 (Wt %) | Comparative Example 2 (Wt %) |
|---|---|---|
| $SiO_2$ | 66.4 | 66.7 |
| $Al_2O_3$ | 1.2 | 1.0 |
| $B_2O_3$ | 11.0 | 10.0 |
| $Na_2O$ | 12.9 | 13.9 |
| $K_2O$ | 0.2 | 0.2 |
| CaO | 4.8 | 5.5 |
| MgO | 3.2 | 2.5 |
| C(acid) | 2.03 | 2.07 |
| C(bio) | 2.09 | 2.13 |
| C(moist) | 3.41 | 3.29 |
| HTV ($10^3$ poise) | 1965° F. | 1949° F. |
| Liquidus | 1738° F. | 1702° F. |

As can be seen from Table 1, the C-ratios of these rotary process glasses indicate that they should both have good performance with respect to acid resistance, moisture resistance, and biosolubility. The Comparative Example 2 glass is reported by the patentee to have a dissolution rate in model physiological saline (composition not disclosed) of 211 ng/cm²/hr. However, examination of the HTV and liquidus temperatures reveals that these differ only by 227° F. and 247° F., respectively. Thus, these glass compositions cannot be used in pot and marble fiberization. These Comparative Examples serve to illustrate the ease with which higher biosolubility can be obtained in rotary processable glass. These glasses cannot be used to manufacture fiberglass by the pot and marble process. However, even were this possible, the flame attenuation and consequent loss of volatile oxides from the fiber surface would be expected to lower the measured biodissolution rate by a factor of from about 2 to 4.

Examples 1 and 2

Two glass formulations were processed into marbles for use in pot and marble fiberization, and glass fibers prepared in the conventional manner. The formulations, C-ratios, HTV ($10^3$ poise), liquidus, and measured biosolubility are presented in Table 2. The ingredients are in mol percent.

TABLE 2

| | Example 1 (mol %) | Example 2 (mol %) |
|---|---|---|
| $SiO_2$ | 67.24 | 67.18 |
| $Al_2O_3$ | 1.04 | 1.02 |
| $B_2O_3$ | 6.08 | 5.99 |
| CaO | 4.99 | 4.87 |
| MgO | 5.24 | 5.26 |
| $Na_2O$ | 15.22 | 15.45 |
| $K_2O$ | 0.26 | 0.23 |
| C(acid) | 2.05 | 2.05 |
| C(bio) | 2.15 | 2.14 |
| C(moist) | 2.89 | 2.87 |
| Biosol K(dis) | 350 | 426 |
| HTV | 1972 | 1981 |
| Liquidus | 1435 | <1325 |

The C-ratios indicate that the glasses of Table 2 should exhibit desirable chemical resistance (both acid and moisture) as well as high biodissolution. The high biodissolution is confirmed by actual tests, being in both cases, considerably greater than 300 ng/cm²/hr.

Example 3, Comparative Examples C3 and C4

A subject invention glass is compared with two commercial glasses for acid resistance and moisture resistance, respectively. The formulations (mol percent) are as follows.

TABLE 3

| | Example 3 | Example C3 | Example C4 |
|---|---|---|---|
| $SiO_2$ | 67.28 | 65.36 | 57.53 |
| $Al_2O_3$ | 1.04 | 1.83 | 3.11 |
| $B_2O_3$ | 6.00 | 4.59 | 7.23 |
| CaO | 4.00 | 6.27 | 8.82 |
| $Na_2O$ | 15.20 | 15.56 | 16.24 |
| $K_2O$ | 0.26 | 0.45 | 0.71 |
| $F_2$ | — | 1.43 | — |
| C(acid) | 2.06 | 1.96 | 1.35 |
| C(bio) | 2.16 | 2.14 | 1.54 |
| C(moist) | 2.89 | 2.67 | 2.11 |
| MgO | 5.23 | 4.52 | 6.36 |

The acid resistance of the Example 3 glass was compared with that of Comparative Example C3. It is noted that the Comparative Example C3 glass meets the C-ratio requirements but not the compositional limitations. The results of the acid resistance test are presented below in Table 3a.

TABLE 3a

| Glass Element | Example 3 Quantity Dissolved (ppm) | Example C3 Quantity Dissolved (ppm) |
|---|---|---|
| Al | 187 | 453 |
| Ca | 2831 | 4110 |
| Mg | 854 | 938 |

To determine moisture resistance, a stress corrosion test is used in which the fibers are stressed by bending in a controlled humidity and temperature test chamber. Fibers which exhibit moisture resistance under these conditions take longer to break. The Example 3 glass was compared to Comparative Example C4 glass, a glass used commercially for building insulation where compression of insulation and storage generates the potential for fiber breakage as a result. After 50 hours, only 12% of the Example 3 glass had broken, while all of the Comparative Example C4 fibers had failed.

Comparative Examples C5 and C6

C-ratios are calculated for the rotary process glasses of Example 3 of U.S. Pat. No. 4,510,252, and Example 2 of U.S. Pat. No. 4,628,038. Composition, calculated C-ratios, liquidus, and estimated HTV ($10^3$ poise) are given below in Table 4, in mol percent.

TABLE 4

| | Example C5 | Example C6 |
|---|---|---|
| $SiO_2$ | 68.2 | 66.67 |
| $Al_2O_3$ | 2.2 | 2.25 |
| $B_2O_3$ | 5.0 | 4.78 |
| $Na_2O$ | 9.2 | 8.68 |
| $K_2O$ | — | 0.26 |
| CaO | 11.9 | 14.77 |
| MgO | 3.5 | 3.60 |
| C(acid) | 1.85 | 1.94 |
| C(bio) | 2.03 | 2.15 |
| C(moist) | 2.54 | 2.70 |

TABLE 4-continued

|  | Example C5 | Example C6 |
|---|---|---|
| HTV ($10^3$ poise), est. | 2280° F. | 2210° F. |
| Liquidus | 1983° F. | 2035° F. |

As can be seen from the table, the acid resistance of Comparative Example C5 is expected to be low, and the biodissolution is expected also to be low, although the glass should display good moisture resistance. However, the difference between HTV ($10^3$ poise) and liquidus is only about 297° F., and thus this glass is not suitable for use in a pot and marble process. The glass of Comparative Example C6 exhibits C(acid) close to an acceptable value, although C(bio) is too high. The glass should have good moisture resistance. However, the glass cannot be used in a pot and marble process as the difference between liquidus and HTV ($10^3$ poise) is only 175° F.

Comparative Example 7

C-ratios and composition data (mol percent) are presented for Example 6 of U.S. Pat. No. 5,108,957.

TABLE 5

|  | Example C7 |
|---|---|
| $SiO_2$ | 69.55 |
| $Al_2O_3$ | 0.08 |
| CaO | 7.46 |
| MgO | 4.30 |
| $Na_2O$ | 15.05 |
| $K_2O$ | 0.04 |
| $B_2O_3$ | 3.52 |
| C(acid) | 2.28 |
| C(bio) | 2.29 |
| C(moist) | 2.72 |
| HTV ($10^3$ poise) | 2003° F. |
| Liquidus | 1706° F. |

The biodissolution for this glass should be marginal, however the moisture and acid resistance should be acceptable. However, the difference in HTV and liquidus ($\Delta T$) indicates that this glass is unsuitable for pot and marble fiberization.

Examples 4–12

Additional glass compositions which fall within the subject invention parameters are presented in the following table.

By the term "consisting essentially of" is meant that additional ingredients may be added provided they do not substantially alter the nature of the composition. Substances which cause the biodissolution rate to drop below 150 $ng/cm^2/hr$ or which lower the $\Delta T$ to a value below 350° F. are substances which do substantially alter the composition. Preferably, the glass compositions are free of iron oxides, lead oxides, fluorine, phosphates ($P_2O_5$), zirconia, and other expensive oxides, except as unavoidable impurities. It should be noted that while rotary process glass compositions are in general unsuitable for pot and marble fiberization, the reverse is not true, and the subject invention glass compositions should yield fibers prepared by the rotary process which have yet higher rates of biodissolution.

Having now fully described the invention, it will be apparent to one of ordinary skill in the art that many changes and modifications can be made thereto without departing from the spirit or scope of the invention as set forth herein.

What is claimed is:

1. Glass fibers exhibiting chemical resistance, moisture resistance, and biosolubility, said glass fibers prepared by pot and marble fiberization and having a shell exterior which has a different composition than the fiber interior, and with the glass fibers being prepared from a glass composition consisting essentially of, in mol percent:

| $SiO_2$ | 66–69.7 |
|---|---|
| $Al_2O_3$ | 0–2.2 |
| RO | 7–18 |
| $R_2O$ | 9–20 |
| $B_2O_3$ | 0–7.1 | said glass composition having a C(acid)$\geq$1.95, a C(bio) $\leq$2.30, a C(moist)$\geq$2.46, a difference, $\Delta T$, between HTV ($10^3$ poise) and liquidus in excess of 350°0 F., and the fibers exhibiting a biodissolution in excess of 150 $ng/cm^2/hr$.

2. The glass fibers of claim 1 wherein said composition consists essentially of, in mol percent:

| $SiO_2$ | 66–69.0 |
|---|---|
| $Al_2O_3$ | 0–2.2 |
| RO | 7–16 |
| $R_2O$ | 9–19 |
| $B_2O_3$ | 0–7.1 |

3. The glass fibers of claim 1 wherein said composition consists essentially of, in mol percent:

EXAMPLES 4–12

|  | Example 4 Mol % | Example 5 Mol % | Example 6 Mol % | Example 7 Mol % | Example 8 Mol % | Example 9 Mol % | Example 10 Mol % | Example 11 Mol % | Example 12 Mol % |
|---|---|---|---|---|---|---|---|---|---|
| $SiO_2$ | 67.28 | 67.4 | 66.38 | 66.9 | 65.96 | 68.03 | 69.08 | 67.96 | 68.61 |
| $Al_2O_3$ | 1.04 | 1.03 | 2.35 | 2.37 | 2.33 | 0 | 0 | 0 | 0 |
| $B_2O_3$ | 6.00 | 6.06 | 3.49 | 7.03 | 6.93 | 0.75 | 3.42 | 3.37 | 6.8 |
| $Na_2O$ | 15.20 | 15.25 | 17.13 | 16.08 | 9.25 | 16.08 | 17.58 | 11.63 | 9.83 |
| $K_2O$ | 0.26 | 0.19 | 0.52 | 0 | 0.51 | 0 | 0 | 0 | 0 |
| CaO | 4.99 | 4.83 | 4.87 | 3.76 | 7.42 | 7.43 | 4.89 | 8.46 | 7.28 |
| MgO | 5.23 | 5.23 | 5.27 | 3.87 | 7.63 | 7.71 | 5.02 | 8.58 | 7.48 |

| | |
|---|---|
| SiO$_2$ | 66–68.25 |
| Al$_2$O$_3$ | 0–2.2 |
| RO | 7–13 |
| R$_2$O | 11–18 |
| B$_2$O$_3$ | 0–7.1. |

4. The glass fibers of claim 1 wherein ΔT is at least about 425° F.

5. The glass fibers of claim 2 wherein ΔT is at least about 425° F.

6. The glass fibers of claim 3 wherein ΔT is at least about 425° F.

7. The glass fibers of claim 1 wherein said fibers have a measured biodissolution rate of greater than 300 ng/cm$^2$/hr.

8. The glass fibers of claim 2 wherein said fibers have a measured biodissolution rate when fiberized by pot and marble fiberization of greater than 300 ng/cm$^2$/hr.

9. The glass fibers of claim 3 wherein said fibers have a measured biodissolution rate of greater than 300 ng/cm$^2$/hr.

10. The glass fibers of claim 4 wherein said fibers have a measured biodissolution rate of greater than 300 ng/cm$^2$/hr.

11. The glass fibers of claim 5 wherein said fibers have a measured biodissolution rate of greater than 300 ng/cm$^2$/hr.

12. The glass fibers of claim 6 wherein said fibers have a measured biodissolution rate of greater than 300 ng/cm$^2$/hr.

13. The glass fibers of claim 1 wherein ΔT is at least about 425° F. and the measured biodissolution is greater than about 400 ng/cm$^2$/hr.

14. The glass fibers of claim 2 wherein ΔT is at least about 425° F. and the measured biodissolution is greater than about 400 ng/cm$^2$/hr.

15. The glass fibers of claim 3 wherein ΔT is at least about 425° F. and the measured biodissolution is greater than about 400 ng/cm$^2$/hr.

16. The glass fibers of claim 1 wherein C(acid)≧2.00, C(bio)≦2.23 and C(moist)≧2.50.

17. The glass fibers of claim 1 wherein C(acid)≧2.00, C(bio)≦2.20 and C(moist)≧2.60.

18. The glass fibers of claim 1, said fibers prepared from a glass composition comprising, in mol percent:

| | |
|---|---|
| SiO$_2$ | 66–69.0 |
| Al$_2$O$_3$ | 0–2.2 |
| RO | 7–16 |
| R$_2$O | 9–19 |
| B$_2$O$_3$ | 0–7.1 | said glass composition having a C(acid)≧2.00, a C(bio)≦2.23, a C(moist)≧2.50, a difference, ΔT, between HTV (10$^3$ poise) and liquidus in excess of 300° F., said fibers exhibiting a biodissolution of greater than about 150 ng/cm$^2$/hr.

19. The fibers of claim 18, wherein said C(acid)≧2.00, said C(bio)≦2.23, said C(moist)≧2.50, said ΔT is greater than about 400° F., said fibers exhibiting biodissolution≧300 ng/cm$^2$/hr.

20. The fibers of claim 18, wherein said glass composition comprises, in mol percent:

| | |
|---|---|
| SiO$_2$ | 66–68.25 |
| Al$_2$O$_3$ | 0–2.2 |
| RO | 7–13 |
| R$_2$O | 11–18 |
| B$_2$O$_3$ | 0–7.1 | said C(acid)≧2.00, said C(bio)≦2.20, said C(moist)≧2.60, said ΔT is greater than about 400° F., said fibers exhibiting biodissolution≧300 ng/cm$^2$/hr.

21. An acid and moisture resistant glass fiber prepared by pot and marble fiberization having a shell exterior which has a different composition than the fiber interior, and with the glass fiber being prepared from a glass composition consisting essentially of, in mol percent:

| | |
|---|---|
| SiO$_2$ | 66.5–67.8 |
| Al$_2$O$_3$ | 0.5–1.5 |
| B$_2$O$_3$ | 5.0–7.0 |
| CaO | 3.0–7.0 |
| MgO | 3.0–7.0 |
| Na$_2$O | 14.0–17.0 |
| K$_2$O | 0.1–0.4 | wherein the sum of CaO and MgO is between about 8.0 and 12.0, said glass fiber exhibiting a ΔT greater than 400° F. and a biodissolution greater or equal to about 350 ng/cm$^2$/hr.

22. A mat containing the glass fibers of claim 1.

23. A mat containing the glass fibers of claim 18.

24. A mat containing the glass fibers of claim 21.

* * * * *